United States Patent
Qamar et al.

(10) Patent No.: US 11,007,287 B2
(45) Date of Patent: May 18, 2021

(54) ACOUSTICALLY EXCITED ENCAPSULATED MICROBUBBLES AND MITIGATION OF BIOFOULING

(71) Applicant: KING ABDULLAH UNIVERSITY OF SCIENCE AND TECHNOLOGY, Thuwal (SA)

(72) Inventors: Adnan Qamar, Thuwal (SA); Luca Fortunato, Thuwal (SA); TorOve Leiknes, Thuwal (SA)

(73) Assignee: KING ABDULLAH UNIVERSITY OF SCIENCE AND TECHNOLOGY, Thuwal (SA)

( * ) Notice: Subject to any disclaimer, the term of this patent is extended or adjusted under 35 U.S.C. 154(b) by 138 days.

(21) Appl. No.: 16/078,315

(22) PCT Filed: Feb. 24, 2017

(86) PCT No.: PCT/IB2017/051099
§ 371 (c)(1),
(2) Date: Aug. 21, 2018

(87) PCT Pub. No.: WO2017/145118
PCT Pub. Date: Aug. 31, 2017

(65) Prior Publication Data
US 2019/0358352 A1 Nov. 28, 2019

Related U.S. Application Data (60) Provisional application No. 62/299,956, filed on Feb. 25, 2016.

(51) Int. Cl.
*A61L 2/025* (2006.01)
*B01D 65/02* (2006.01)
(Continued)

(52) U.S. Cl.
CPC .............. *A61L 2/025* (2013.01); *B01D 65/02* (2013.01); *B01D 65/08* (2013.01); *B01J 13/04* (2013.01);
(Continued)

(58) Field of Classification Search
CPC ......... A61L 2/025; B01D 65/02; B01D 65/08; B01D 61/10; B01D 61/20; B01D 2311/04;
(Continued)

(56) References Cited

U.S. PATENT DOCUMENTS

| 4,572,203 A | 2/1986 | Feinstein |
| 5,552,133 A | 9/1996 | Lambert et al. |

(Continued)

FOREIGN PATENT DOCUMENTS

WO 2015079062 A1 6/2015

OTHER PUBLICATIONS

Communication pursuant to Article 94(3) EPC in corresponding/related European Application No. 17712235.5, dated Jun. 3, 2019 (Documents D1 and D2 were cited in the IDS filed Aug. 21, 2018).
(Continued)

*Primary Examiner* — Timothy C Cleveland
(74) *Attorney, Agent, or Firm* — Patent Portfolio Builders PLLC (57) ABSTRACT

Provided herein is a universally applicable biofouling mitigation technology using acoustically excited encapsulated microbubbles that disrupt biofilm or biofilm formation. For example, a method of reducing biofilm formation or removing biofilm in a membrane filtration system is provided in which a feed solution comprising encapsulated microbubbles is provided to the membrane under conditions that allow the encapsulated microbubbles to embed in a biofilm. Sonication of the embedded, encapsulated
(Continued)

microbubbles disrupts the biofilm. Thus, provided herein is a membrane filtration system for performing the methods and encapsulated microbubbles specifically selected for binding to extracellular polymeric substances (EFS) in a biofilm.

10 Claims, 3 Drawing Sheets

(51) Int. Cl.
| | |
|---|---|
| *B01D 65/08* | (2006.01) |
| *B01J 13/04* | (2006.01) |
| *B01D 61/10* | (2006.01) |
| *B01D 61/20* | (2006.01) |

(52) U.S. Cl.
CPC .............. *B01D 61/10* (2013.01); *B01D 61/20* (2013.01); *B01D 2311/04* (2013.01); *B01D 2311/25* (2013.01); *B01D 2315/20* (2013.01); *B01D 2321/18* (2013.01); *B01D 2321/2075* (2013.01)

(58) Field of Classification Search
CPC ............ B01D 2311/25; B01D 2315/20; B01D 2321/18; B01D 2321/2075; B01D 61/368; B01J 13/04; F28F 19/00; F28G 7/00; F28G 13/00; B08B 3/102; B08B 3/13; B08B 17/00
See application file for complete search history.

(56) References Cited

U.S. PATENT DOCUMENTS

| | | | |
|---|---|---|---|
| 7,008,540 B1* | 3/2006 | Weavers | B01D 63/02 210/321.69 |
| 7,632,413 B2* | 12/2009 | Cordemans De Meulenaer | A61L 2/025 210/748.03 |
| 2005/0241668 A1* | 11/2005 | Trampuz | A61L 2/02 134/1 |
| 2008/0237028 A1 | 10/2008 | Kislev | |
| 2010/0239627 A1 | 9/2010 | Whitekettle et al. | |

OTHER PUBLICATIONS

Communication pursuant to Article 94(3) EPC in corresponding/related European Application No. 17712235.5, dated Jun. 17, 2020.
Cochran, S., et al., "Sonoluminescence as an indicator of cell membrane disruption by acoustic cavitation," Ultrasound in Medicine and Biology. Jun. 2001. (Abstract Only).
Goldberg, B.B., et al., "Ultrasound contrast agents: a review," Ultrasound Medicine and Biology. Jan. 1994. '(Abstract Only).
Kim, T.H., et al., "Biofilm formation and its effects on biofouling in RO membrane processes for wastewater reuse," Desalination and Water Treatment. Aug. 2012. (Abstract Only).
Al-Ahmad, M., et al., "Biofuoling [sic] in RO membrane systems—Part 1: Fundamentals and control," Desalination, vol. 132, Issues 1-3, Dec. 20, 2000 (Presented at the Conference on Membranes in Drinking and Industrial Water Production, Paris, France, Oct. 3-6, 2000), pp. 173-179.
Baker, J.S., et al., "Biofouling in membrane systems—A review," Desalination, vol. 118, Issues 1-3, Sep. 20, 1998 (Presented at the Conference on Membranes in Drinking and Industrial Water Production, Amsterdam, Sep. 21-24, 1998), pp. 81-89.
Liu, H., et al., "Extraction of extracellular polymeric substances (EPS) of sludges," Journal of Biotechnology, vol. 95, No. 3, May 23, 2002, pp. 249-256.
London, F., "The General Theory of Molecular Forces," Transactions of the Faraday Society, vol. 33, Jan. 1, 1937, pp. 8-26.
Prentice, P., et al., "Membrane disruption by optically controlled microbubble cavitation," Nature Physics, vol. 1, Nov. 2005 (Published online Oct. 23, 2005), pp. 107-110.
Qamar, A., et al., "A Model for an Acoustically Driven Microbubble Inside a Rigid Tube," Journal of Fluids Engineering, vol. 137, Feb. 2015, pp. 021301-1-021301-9.
Damar, A., et al., "Dynamics of micro-bubble sonication inside a phantom vessel," Applied Physics Letters, vol. 102, Jan. 7, 2013 (Published online Jan. 10, 2013), pp. 013702-1-013702-5 (6 pages provided).
Qamar, A., et al., "Evolution of Acoustically Vaporized Microdroplets in Gas Embolotherapy," Journal of Biomechanical Engineering, vol. 134, Mar. 2012, pp. 031010-1-031010-13.
Silalahi, S.H.D., et al., "Cleaning strategies in ceramic microfiltration membranes fouled by oil and particulate matter in produced water," Desalination, vol. 236, Jan. 2009 (Presented at the International Membrane Science and Technology Conference, IMSTEC 07, Sydney, Australia, Nov. 5-9, 2007), pp. 160-169.
The Dow Chemical Company ("DOW"), "Dow—Water & Process Solutions, FILMTECTM Reverse Osmosis Membranes, Technical Manual," 2014, pp. 1-181.
Whittaker, C., et al., "Evaluation of Cleaning Strategies for Removal of Biofilms from Reverse-Osmosis Membranes," Applied and Environmental Microbiology, vol. 48, No. 3, Aug. 1984, pp. 395-403.
Wong, Z.Z., et al., "Bubble evolution in acoustic droplet vaporization at physiological temperature via ultra-high speed imaging," Soft Matter, vol. 7, Mar. 3, 2011, pp. 4009-4016.
International Search Report in related International Application No. PCT/IB2017/051099, dated May 24, 2017.
Radziuk, D., et al., "Ultrasonic Mastering of Filter Flow and Antifouling of Renewable Resources," ChemPhysChem Reviews—A European Journal of Chemical Physics & Physicalchemistry, Jan. 6, 2016, vol. 17, pp. 931-953.
Written Opinion of the International Searching Authority in related International Application No. PCT/IB2017/051099, dated May 24, 2017.
Communication pursuant to Article 94(3) EPC in corresponding/related European Application No. 17712235.5, dated Feb. 26, 2021.

\* cited by examiner

ACOUSTICALLY EXCITED ENCAPSULATED MICROBUBBLES AND MITIGATION OF BIOFOULING

RELATED APPLICATION DATA

This application is a U.S. National Stage of International Application No. PCT/IB2017/051099, filed on Feb. 24, 2017, which claims the benefit of U.S. Provisional Patent Application Ser. No. 62/299,956, filed Feb. 25, 2016, the entire contents of which are incorporated herein by reference.

TECHNICAL FIELD

The present invention relates to a method and system for preventing biofilm formation or removing biofilm.

BACKGROUND OF THE INVENTION

The background of this invention will address biofilm formation and removal, as well as membrane technology matters.

Biofilm Formation and Biofouling

Microorganisms are microscopic living organisms that are found in all areas of the biosphere in enormous numbers. Bacteria make up a large portion of these microorganisms and are among the most abundant organisms on earth. Bacteria possess a wide range of metabolic versatility and adaptability allowing them to thrive in many circumstances where other organisms could not survive.

Bacteria can exist as individual organisms, but the majority live in colonies consisting of an aggregation of numerous bacterial organisms. One of the mechanisms employed by bacterial colonies, as well as other microorganisms, is the production of extracellular polymeric substances that produce a slime-like covering over the colonies. These aggregated microorganisms usually exist in nature by attaching to and growing upon living or inanimate surfaces. A common feature of this attached aggregated growth state is that the cells develop a biofilm. Biofilm formation is a process whereby microorganisms attach to and grow on a surface and produce extracellular polymers that facilitate attachment and matrix formation.

A biofilm is a bacterial aggregation on a surface with a structure that includes bacterial cells and a matrix of bacterially produced extracellular polymeric substances (EPS), along with biogenic and inorganic particles. Extracellular polymeric substances EPS, which are primarily composed of proteins, polysaccharides, and nucleic acids, plays a vital role in biofilm growth and development. As a result, the extracellular polymeric substances EPS can alter the density, porosity, charge, water content, and sorption properties of the biofilm with time.

Additionally, extracellular polymeric substances EPS enhances the mechanical strength and adhesiveness of the biofilm through electrostatic attraction, hydrogen bonding and London dispersion forces. Thus, biofilm structural integrity, adhesiveness and elasticity make biofilms resilient and difficult to remove from surfaces. The presence of divalent cations, such as magnesium and calcium, can form salt bridges, for example, between negatively charged bacteria and a surface such as a membrane surface. The structure and charges of the biofilm and the EPS thus help to protect the aggregated bacteria or other microorganisms from applied biocides.

Biofouling is the gradual accumulation of organisms on surfaces to the detriment of the function of the surface, and of particular relevance herein are those organisms that produce biofilms. Biofilm formation is caused by the accumulation of microorganisms and extracellular polymeric substances (EPS) produced by the microorganisms. Biofilms can form on a variety of surfaces including membranes (e.g., in membrane filtration systems), heat exchangers, medical devices, paper manufacturing systems, food processing systems, and in underwater construction. Biofilm formation, which occurs frequently in membrane filtration systems, causes biofouling, which is an unacceptable decline in membrane performance. Additionally, a hydrodynamic boundary layer generally exists adjacent to the biofilm which reduces the flow of the feed water over the biofilm, thereby decreasing the ability of the feed water to dislodge the biofilm.

The development and rate of biofouling depends on the quality of the feed water supplied to a membrane filtration unit. Feed water typically contains microorganisms (e.g., algae, bacteria, fungi) with nutrient and energy sources that can stimulate the growth of bacterial colonies and the formation of biofilm on the surface of a membrane. Biofouling is a major problem in all membrane filtration systems, for example accounting for about 35% of membrane failures in reverse osmosis (RO) plants. Thus, biofouling presents significant challenges and costs wherever it occurs, but especially in membrane filtration systems. Simply put, a membrane is a selective barrier with a partial permeability—it will allow certain substances to pass through the barrier, while preventing other substances from doing so.

Membrane Technology

A membrane is usually defined by a discrete, thin interface that moderates the permeation of chemical species in contact with it. The substances that can pass through, or be prevented from passing through, the membrane interface may be molecules, ions or other small particles. The influent of an artificial membrane is known as the feed-stream, the liquid that passes through the membrane is known as permeate or filtrate, and the liquid containing the retained constituents (substances that are prevented from passing through the membrane) is the retentate or concentrate. A normal filter meets this definition of a membrane, but, by convention, the term membrane is usually limited to structures that permeates dissolved or colloidal species, whereas the term filter is used to designate structures that separate larger-sized particulate suspensions.

Membranes can be generally classified into two classes: synthetic membranes and biological membranes. Biological membranes include cell membranes (outer coverings of cells or organelles that allow passage of certain constituents), nuclear membranes, which cover a cell nucleus, and tissue membranes, such as mucosae or serosae. Synthetic membranes are made by humans for use in laboratories or industry, such as chemical plants.

Synthetic membranes show a large variety in their physical structure and the materials from which they are made. Based on their structure they can be classified into four groups: (1) porous membranes, (2) homogeneous solid membranes, (3) solid membranes carrying electrical charges, and (4) liquid or solid films containing selective carriers. The materials used for the preparation of membranes can be polymers, ceramics, glass, metals, or liquids, and the materials may be neutral or carry electrical charges (for example, fixed ions).

There are several historical limitations involved with the application, use and manufacture of known membrane processes. A major disadvantage involved with the use of known membranes, especially in water- and wastewater-treatment processes, is that the long-term reliability has not completely been proven. Membrane processes sometimes require excessive pretreatment due to their sensitivity to concentration polarization, chemical interaction with water constituents, and membrane fouling. And, membranes have historically been mechanically unreliable and non-robust, which means membranes can easily be destroyed by a malfunction in the operating procedure.

Depending on the composition of the feed solution and the required quality of the product water, a combination of membrane or filtration processes may be appropriate. For example, if ultrapure water for certain industrial applications is required, a sequence of membrane filtration processes may be applied, such as reverse osmosis, ion exchanger, UV sterilization, and microfiltration as a point-of-use filter to remove traces of particles. In certain applications, such as the purification of industrial effluents and wastewaters or the desalination of brackish water, there may be a problem with the disposal of the concentrate. In these applications, brine post-treatment procedures may need to be applied to the concentrate.

Membrane biofouling occurs heterogeneously on membrane surfaces and often occurs in the first element of the pressure vessel in reverse osmosis (RO) systems, for example. In RO systems, biofilm can form over the course of a few days to a few weeks. In a feed that is biologically active, a short timeline is common, e.g. 3-5 days from inoculation.

Biofouling Control and Biofilm Removal

Although membrane biofouling is common, there has been very limited success in prevention or remediation of biofouling due to membrane sensitivity to chemical/biological processes, site-specific feed water quality issues, and the like. In the prior art, no universal technology exists that can be applied to all sorts of feed water, as feed water quality varies in terms of bacteria levels, pH and in the analysis of both organic and inorganic compounds.

One conventional approach to biofouling control includes the use of biocides and disinfectants, which have achieved very limited success. Chlorine as a disinfectant is widely applied in water treatment, but it has significant limitations in membrane systems. Polymeric membranes, which are commonly used in water treatment, are prone to chemical oxidation and degradation by chlorine; thus, in such uses, chlorine must be removed from the feed water prior to entering the membrane section, and chlorine fails to reach bacterial colonies on the membrane. Furthermore, chlorine can break down natural organic matter (NOM) present in the feed water, creating a nutrient source to the microorganisms present Apart from chlorine, non-oxidizing biocides are available such as DBNPA (2,2-dibromo-3-nitrilopropionamide) and isothiazalones. Dose rates and application costs for these chemicals are high and are not approved for online dosing in potable applications. Furthermore, these available biocide products are unable to adequately penetrate biofilm layers and lyse/dissolve the foulants within the biofilm.

Membrane cleaning-in-place procedures are mechanical and chemical operations used for disrupting and removing existing biofilm layers. In practice, such processes are inadequate to remove biomass from membrane surfaces. These procedures require plugging of the feed path, which restricts transport of the chemicals into the blocked region. The use of cleaning-in-place is further limited due to several factors, such as mechanical interaction, cost, incorrect chemical selection, inability to penetrate the biofilm layer, poor cleaning practice (with respect to parameters such as pH, temperature, contact time or improper recirculation flow rates) and delays in application.

Recent control technologies primarily focus on limiting biofouling by extensive pretreatment of the feed water to minimize system bacteria and nutrient/energy sources. Current use of membrane technologies, such as microfiltration (MF) or ultrafiltration (UF), has been used for pretreatment with reverse osmosis (RO) systems with little success. These techniques are rarely 100% efficient, and a small percentage of viable bacteria pass through the pretreatment membranes to the RO system, and the MF/UF filtration systems themselves are also susceptible to biofouling. There exists a long-felt, unfulfilled need for a safe, efficient and cost-effective cleaning-in-place method for mitigation of biofouling by prevention or removal of biofilms.

SUMMARY OF THE INVENTION

Provided herein is a biofouling mitigation technology that is universally applicable to membrane filtration systems. More specifically, the methods described herein comprise the use of acoustically excited encapsulated microbubbles to disrupt biofilms, such as methods and systems for reducing biofilm formation or removing biofilm. The methods include providing a feed solution, wherein the feed solution comprises encapsulated microbubbles under conditions that allow the encapsulated microbubbles to embed in a biofilm along the path of the feed solution. The methods further include sonicating the embedded, encapsulated microbubbles under conditions that disrupt the biofilm.

The present invention may use encapsulated microbubbles comprising a gas core and an encapsulation shell comprising a ligand of lipid, protein, polymer, or any other suitable ligand, wherein the ligand binds one or more extracellular polymeric substances (EPS) in a biofilm. The present invention may also use a membrane filtration system comprising a feed solution stream, wherein the feed solution comprises encapsulated microbubbles; a membrane for filtering the feed solution stream, and a transducer for applying ultrasonic waves to the feed solution stream, the membrane, or both, wherein the transducer is configured to provide ultrasonic waves of a selected frequency and amplitude, wherein the frequency and amplitude does not cause acoustic cavitation of the encapsulated microbubbles.

The present invention also covers a method to recycle the retentate solution containing the disrupted biofilm by increased sonication of the retentate solution to cause cavitation of the encapsulated microbubbles and sonoluminescence of the retentate. High-intensity ultrasound drives the microbubbles to their acoustic cavitation thresholds and ultimately to sonoluminescence (extreme thermal shock, on a very short timescale), killing microorganisms from the uprooted biofilm near the microbubbles. Cavitation and sonoluminescence also destroys the microbubbles, such that the retentate is free or relatively free from remaining gas, leaving only shell material (e.g., lipid, protein, polymer, or ligand) along with EPS and other organic/inorganic compounds. The treated retentate can be recycled to the feed solution or discarded.

The details of one or more embodiments are set forth in the description below. As used throughout, the methods are described for use in membrane filtration systems, but the methods described in the present invention may also be useful in any system or surface where there is biofilm formation. Other features, objects, and advantages will be apparent from the description and from the claims.

BRIEF DESCRIPTION OF THE DRAWINGS

The above, and other objects and advantages of the present invention will be understood upon consideration of the following detailed description taken in conjunction with the accompanying drawings, in which like reference characters refer to like parts throughout, and in which.

While the invention is susceptible to various modifications and alternative forms, specific embodiments thereof have been shown by way of example in the drawings and are herein described in detail. It should be understood that the description herein of specific embodiments is not intended to limit the invention to the particular forms disclosed, but on the contrary, the intention is meant to cover all modifications, equivalents, and alternatives falling within the spirit and scope of the invention as defined by the appended claims.

DETAILED DESCRIPTION

As described herein, the present invention is a method of mitigating biofouling using acoustically excited microbubbles. The present biofouling mitigation technology can be applied to any quality of feed water and does not involve addition of biocides and/or feed water pretreatment. The present invention is an alternative cleaning-in-place technique that can be electronically controlled.

Provided herein is a method of reducing biofilm formation or removing biofilm in a membrane filtration system, where the method comprises the steps of providing a feed solution to a membrane filtration system, wherein the feed solution comprises encapsulated microbubbles under conditions that allow the encapsulated microbubbles to embed in a biofilm in the membrane filtration system, and sonicating the encapsulated microbubbles in the membrane filtration system under conditions that prevent or disrupt biofilm or biofilm formation. The encapsulated microbubbles are added to the feed solution either continuously or intermittently. The addition of the encapsulated microbubbles can be accomplished, for example, by a separate encapsulated microbubble feed line or into the feed line for feed solution to be filtered.

The present invention uses low-frequency sound waves (ultrasound range) to drive encapsulated microbubbles embedded in the biofilm structure to oscillate during expansion and contraction because of their compressible gas cores. Under resonating conditions, these encapsulated microbubbles rapidly expand and contract (approximately 5-10 times of initial radius) with oscillations, thus rupturing the biofilm from a surface.

The sonicating step comprises, for example, applying sonic waves with a transducer to the surface of the membrane filtration unit at the resonate frequency of the encapsulated microbubbles. The sonicating step optionally includes applying ultrasonic waves or sinusoidal pressure waves to the target surface or membrane filtration unit to be treated. The ultrasonic waves applied are within a range applicable to the size of the microbubbles. The ultrasonic waves are optionally selected from the range of 100 KHz to 3 MHz with amplitude ranging between 1-5 MPa for microbubbles of 5-50 microns.

The acoustic intensity is further selected based on local hydrodynamics and material properties so as to achieve the desired oscillation. The acoustic waves are provided so as to cause the encapsulated microbubbles to oscillate (i.e., expand and collapse) so as to generate shear and thermal gradients sufficient to damages the biofilm. The oscillation is controlled primarily by the applied acoustic frequency and amplitude. For a free bubble, the natural resonating frequency (i.e., corresponding to maximization of bubble growth and collapse) is calculated with the following equation:

$$f = \frac{1}{2\pi R}\sqrt{\frac{3\gamma P}{\rho}}$$

where R is the initial bubble size, P the ambient pressure, $\rho$ the density of the surrounding fluid, and $\gamma$ the specific heat ration of gas.

The disclosed method is useful for a variety of surfaces, including, but not limited to, membrane surfaces. More specifically, the method is useful with polymeric membranes and ceramic membranes such as, but are not limited to, membranes comprising cellulose acetate (CA), nitrocellulose (CN), cellulose esters (CE), polysulfone (PS), polyether sulfone (PES), polyacrilonitrile (PAN), polyvinylidiene fluoride (PVDF), polypropylene (PP), polyethylene (PE), polyvinyl chloride (PVC), polytetrafluoroethylene (PTFE), polyamide (PA), or (polyimide PI). Ceramic membranes include, but are not limited to, membranes comprising alumina, titania, zirconia oxides, silicon carbide or other glass-like material.

The method is also useful in a variety of membrane filtration systems including reverse osmosis systems (RO), microfiltration systems (MF), ultrafiltration systems (UF), nano-filtration systems (NF), forward osmosis systems (FO), and membrane distillation (MD) systems. The membrane filtration system can be in several configurations (e.g., spiral wound, tubular, hollow fiber, flat sheet, etc.). The membrane filtration system can be submerged or pressurized, and membrane thicknesses (while they depend on the system implementation) will range from 0.01 microns to 1000 microns, with 0.1 microns to 10 micron being a preferred thickness range for most water treatment systems.

The membrane in the present invention may be made of synthetic organic polymers where the MF and UF types of membranes are often made from the same materials, but they are produced under different membrane formation conditions so that different pore sizes are produced. Typical MF and UF polymers for membrane used in the present invention include poly(vinylidene fluoride), polysulfone, poly (acrylonitrile) and poly(acrylonitrile)-poly(vinyl chloride) copolymers. Poly (ether sulfone) can also be used for UF membranes used with the present invention. MF membranes can also include cellulose acetate-cellulose nitrate blends, nylons, and poly(tetrafluoroethylene). RO membranes are typically either cellulose acetate or polysulfone coated with aromatic polyamides. NF membranes are made from cellulose acetate blends or polyamide composites like the RO membranes, or they could be modified forms of UF membranes such as sulfonated polysulfone.

The feed solution is selected from the group consisting of fresh water, ground water, brackish water, sea water, waste water, and industrial water. This method is useful regardless of the quality of the feed source. By way of example, the methods provided herein are useful in water desalination and water reclamation/reuse systems. Low feed water flow rates for this example include relatively low feed water operating pressure are approximately 100 to 400 kPa (15 to 60 psi), while this system can be used with higher operating pressure of approximately 200 to 700 kPa (30 to 100 psi). Biofouling and biofilms accumulated on the membrane can include bacterial cells and a matrix of bacterially produced extracellular polymeric substances (EPS), along with biogenic and inorganic particles. Extracellular polymeric substances EPS, which are primarily composed of proteins, polysaccharides, and nucleic acids, plays a vital role in biofilm growth and development. As a result, the extracellular polymeric substances EPS can alter the density, porosity, charge, water content, and sorption properties of the biofilm with time.

Extracellular polymeric substances EPS enhances the mechanical strength and adhesiveness of the biofilm through electrostatic attraction, hydrogen bonding and London dispersion forces. Thus, biofilm structural integrity, adhesiveness and elasticity make biofilms resilient and difficult to remove from surfaces. The presence of divalent cations, such as magnesium and calcium, can form salt bridges, for example, between negatively charged bacteria and a surface such as a membrane surface. The structure and charges of the biofilm and the EPS thus help to protect the aggregated bacteria or other microorganisms from applied biocides.

The encapsulated microbubbles used herein comprise a gas core (e.g., air, or heavy gases like perfluorocarbon, or nitrogen) that forms the majority of the particle volume, and an encapsulation shell comprising a lipid (e.g., mannosylerythritol lipids or the like), protein (e.g., serum such as Bovine serum, human serum, or the like) or polymer (e.g., poly-L-lysine, ethylene glycol, or the like), or other ligand capable of binding extracellular polymeric substances. Microbubbles used in the present invention are usually sized less than 1 micrometer (μm), and preferably range in size from 0.5 μm to 10 μm for use in the present invention.

The lipid, protein, polymer, or other ligand encapsulating the microbubbles binds to one or more extracellular polymeric substances (EPSs) in a biofilm. The specific lipid, protein, polymer, or other ligand material forming the outer shell is selected based on the particular use. Furthermore, the encapsulation allows specific binding to the growing biofilm, provides stability to the gas core, and prevents coalescence of the microbubbles.

The encapsulated microspheres are, preferably, 5-50 microns in diameter, but this diameter may be varied by a predetermined amount without departing from the scope of the invention. Encapsulated microbubbles in the form of contrast agents are used for various applications such as perfusion, molecular imaging, drug delivery, thrombus dissolution, gas embolotherapy, sonoporation, and micro-pumping in different biological and biomedical applications. Preferably, the encapsulated microbubble production device includes a source for mechanical agitation or sonication.

The production device may also be connected to the feed line or a feed solution storage chamber to supply the microbubbles to the feed solution prior to the membrane exposure. Microbubbles used in the present invention are usually sized less than 1 micrometer (m), and preferably range from 5-50 microns in diameter size or from 0.5 μm to 10 μm for use in the present invention.

The method optionally further comprises collecting a retentate comprising the disrupted biofilm and the encapsulated microbubbles. The retentate is optionally treated with acoustic waves (e.g., ultrasonic waves), wherein the acoustic waves causes cavitation of the encapsulated microbubbles and sonoluminescence of the retentate. As the retentate contains the uprooted biofilm and attached microbubbles, high-intensity ultrasound drives the microbubbles to their acoustic cavitation thresholds and ultimately to sonoluminescence (extreme thermal shock, on a very short timescale).

The sonoluminescence kills the microorganisms near the microbubbles. The retentate, now devoid or relatively devoid of microorganisms, can then be reused, partially or completely, by recycling the retentate to the feed solution or can be properly disposed. Cavitation and sonoluminescence also destroys the microbubbles, such that the retentate is free or relatively free from remaining gas, leaving only shell material (e.g., lipid, protein, polymer, or ligand) along with EPS and other remaining organic/inorganic compounds. The treated retentate can be recycled to the feed solution or discarded.

Figure 1:
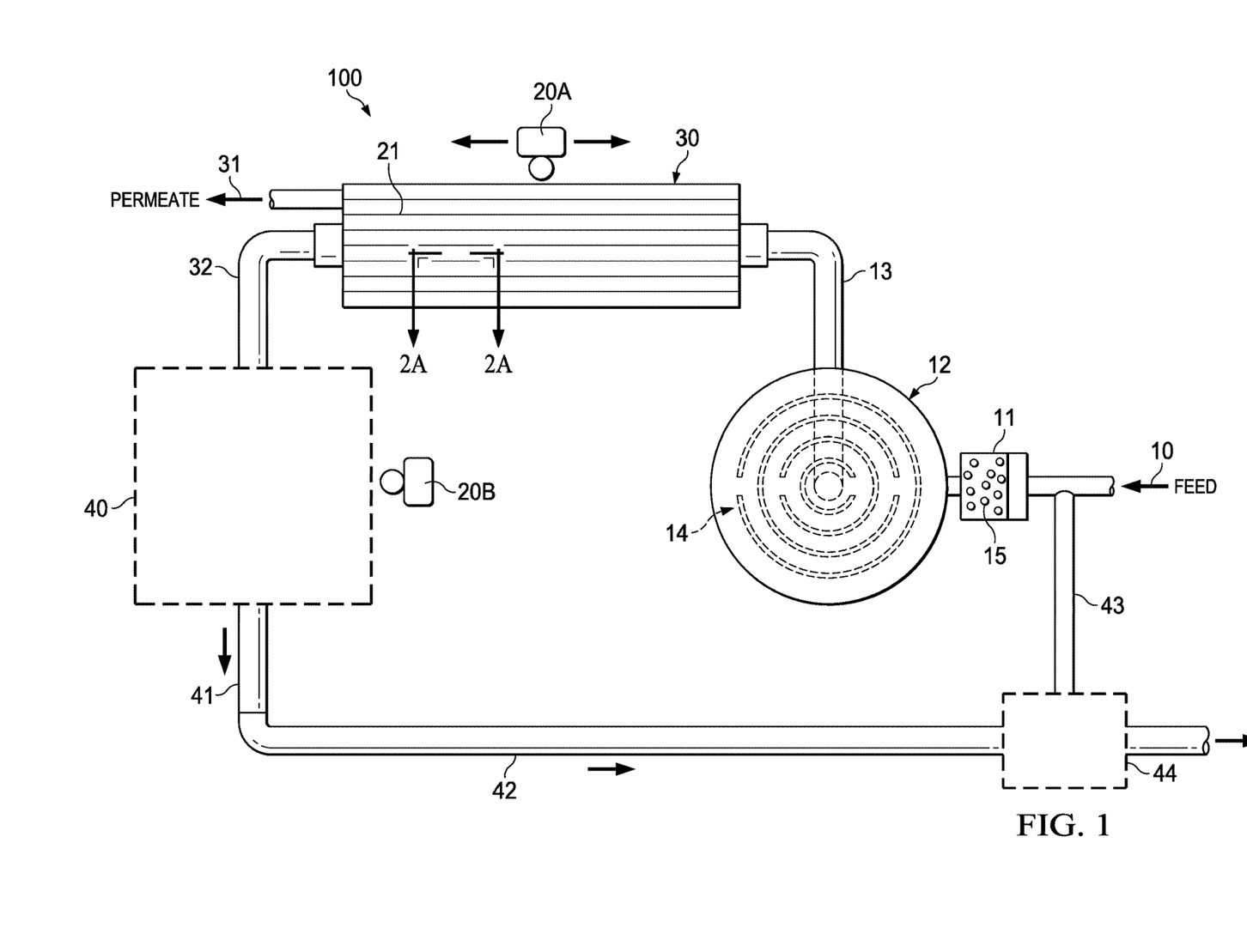
FIG. 1 is a schematic of an exemplary membrane filtration system.

Also provided is a membrane filtration system used in the methods described herein, an example of which is shown in FIG. 1. As shown in FIG. 1, the membrane filtration system (100) comprises a feed solution stream (10) with encapsulated microbubbles (15) produced, for example, by a microbubble production unit (11); a membrane (21) or set of membranes, for example, in a membrane filtration unit (30) for filtering the feed solution stream (10); and a first transducer (20A) for applying ultrasonic waves to the feed solution stream, the membrane, or both.

The feed solution stream (10) brings the feed solution to the microbubble production unit (11) where the microbubbles (15) are added to the feed solution. The feed solution stream then carries the feed solution and the microbubbles (15) to the membrane filtration unit (30). The membrane (21) within the membrane filtration unit (30) is where biofilm is most likely to occur, and the microbubbles (15) will flow across the membrane (21) and become embed in the biofilm attached to the membrane surface. The first acoustic transducer (20A) is situated to provide sonic waves to the biofilm with the embedded microbubbles on the membrane surface.

The acoustic transducer (20A) is mounted in either sweeping configuration (e.g. single transducer, automatically scanning the membrane unit) or long hydro-filament transducers (sonar) embedded in the membrane module. These transducer configuration designs eliminate any mechanical involvement as an acoustic pulse can then be easily triggered by an electric signal from a control system.

The first acoustic transducer (20A) is configured to provide ultrasonic waves of selected frequency and amplitude. The frequency and amplitude are selected to avoid acoustic cavitation of the encapsulated microbubbles. By way of example, the selected frequency is selected from the range of 100 KHz to 3 MHz and the amplitude is less than 5 MPa, less than 4 MPa, less than 3 MPa, less than 2 MPa, or less than 1 MPa for microbubbles of about 5-50 microns. However, any range of frequency or amplitude can be selected within the ranges so as to avoid acoustic cavitation of the encapsulated microbubbles.

The system may also include a mixing tank (12), which has baffles (14) to promote mixing of the feed solution and the encapsulated microbubbles, and a flow outlet (13) to deliver the encapsulated microbubbles (15) and feed solution stream (10) to the membrane filtration unit (30). In FIG. 1, the mixing tank (12) and baffles (14) are shown in place in the membrane filtration system (100). The mixing tank (12) is situated adjacent the microbubble production unit (11) along the feed solution stream (10) and prior to the membrane filtration unit (30). Turbulence created by the solution flowing across the baffles (14) within the mixing tank (12) promotes mixing of the microbubbles (15) with the feed solution. The mixture of feed solution and microbubbles is then delivered to the membrane filtration unit (30) via the feed stream inlet (13).

The microbubble solution is optionally external to the system. In such case, the system includes a separate feed line (not shown) for delivering encapsulated microbubbles to the feed stream prior to entering the membrane filtration unit. The present invention system also includes a permeate, or filtrate, stream (31), and a retentate, or concentrate, stream (32). The permeate and retentate streams exit the membrane filtration unit (30) after the feed solution has encountered the filtration membrane (21) and the first transducer (20A). Microbubbles used in the present invention are usually sized less than 1 micrometer (μm), and preferably range in size from 0.5 μm to 10 μm for use in the present invention.

Permeate, or filtrate, is the liquid that passes through, or permeates, the membrane and is devoid of the constituents that were prevented from passing through the membrane. The system optionally includes a first collector (not shown) to receive the permeate or filtrate from the permeate stream (31). The permeate exits the membrane filtration unit (30) via permeate stream (31).

Retentate, or concentrate, is the liquid containing the retained constituents that were prevented from passing through the membrane. The retentate exits the membrane filtration unit (30) via the retentate stream (32) and contains the ruptured biofilm and microbubbles in addition to the retained constituents.

The system optionally includes a second collector (40) for collecting retentate via retentate stream (32). The system can further include a second transducer (20B) for applying ultrasonic waves to the retentate in the second collector (40).

This second transducer (20B) is configured to provide ultrasonic waves of a selected frequency and amplitude, wherein the frequency and amplitude cause acoustic cavitation of the encapsulated microbubbles. The cavitation of the encapsulated microbubbles serves to destroy the microorganisms and disrupt the biofilm sufficiently to discard or recycle to the feed solution all or a portion of the retentate.

The acoustic transducer (20B) can be mounted in either sweeping configuration (e.g. single transducer, automatically scanning the second collector unit) or long hydrofilament transducers (sonar) in the second collector unit. These transducer configuration designs eliminate any mechanical involvement as an acoustic pulse can then be easily triggered by an electric signal from a control system.

The system further includes a retentate line (42) that leads from the second collector (40) via an outlet for the retentate stream (41) to a dumping station (44). Optionally or additionally, the system employs a recycle line (43) which recycles the retentate treated by the second transducer (20B) back to the feed solution stream (10).

The system may further include a control system, which directs the membrane filtration system. Controlled operations optionally include, for example, feed volume and speed; production rate and size of the microbubbles; number and frequency, amplitude, and duration of the transducer(s) signal; amount of recycled retentate; and the like.

Figures 2A, 2B:
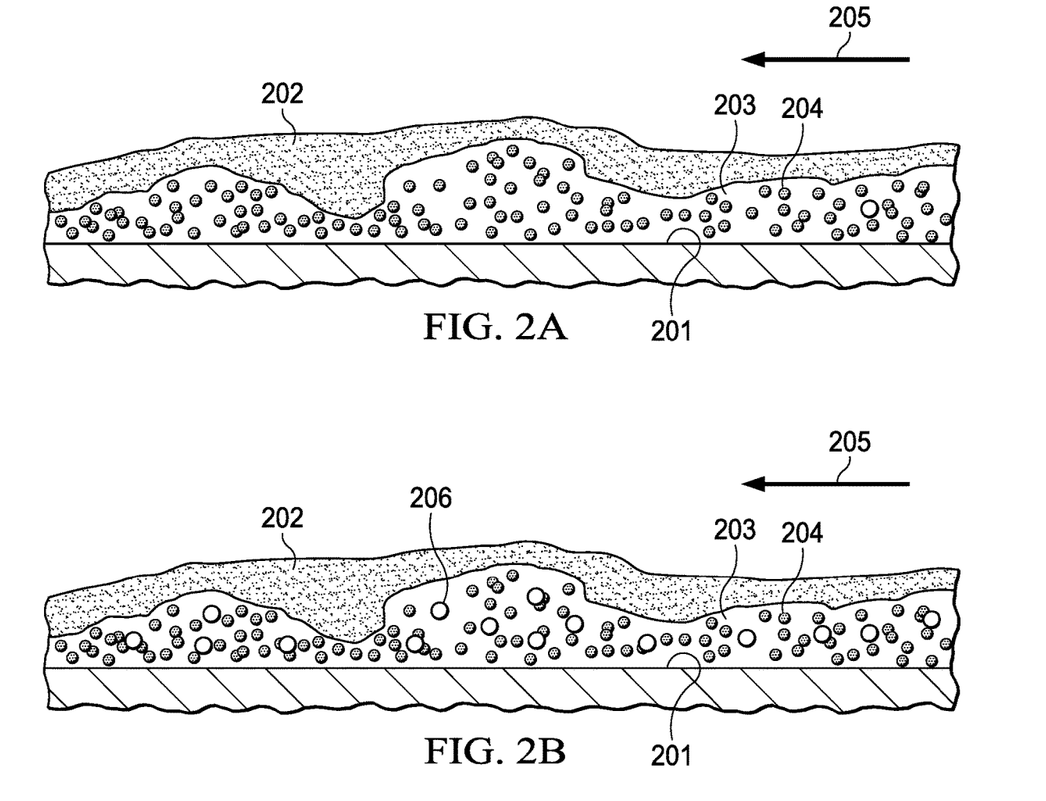
FIG. 2A is a schematic of a cross-section of a membrane filter with a biofilm on the surface of the membrane.
FIG. 2B is a schematic of a cross-section of a membrane filter with a biofilm on the surface of the membrane, wherein the biofilm entraps embedded encapsulated microbubbles.
Figure 2C:
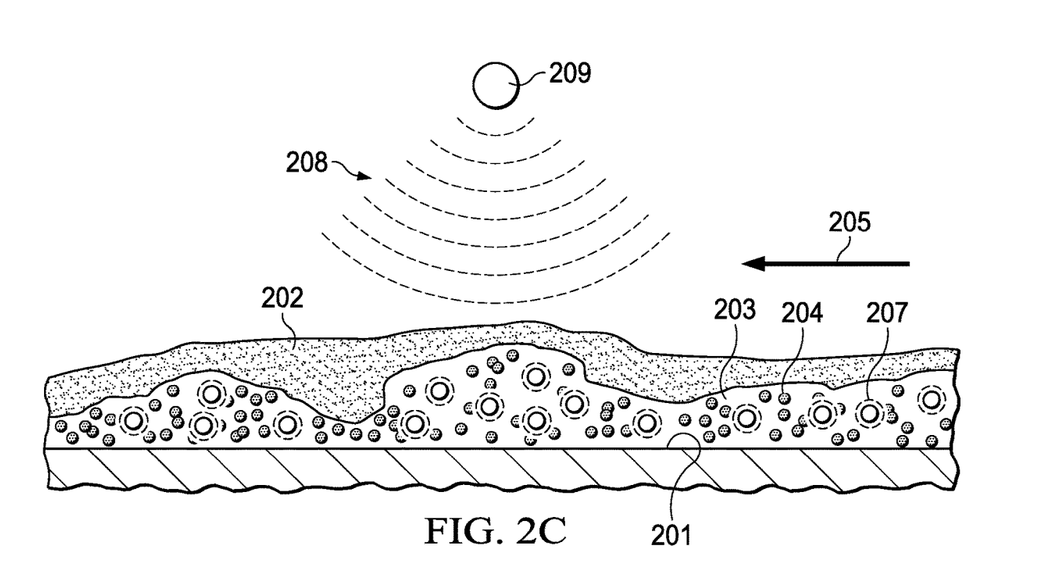
FIG. 2C is a schematic of a cross-section of a membrane filter with a biofilm on the surface of the membrane, wherein the biofilm contains embedded encapsulated microbubbles acoustically excited by an ultrasound transducer.
Figure 2D:
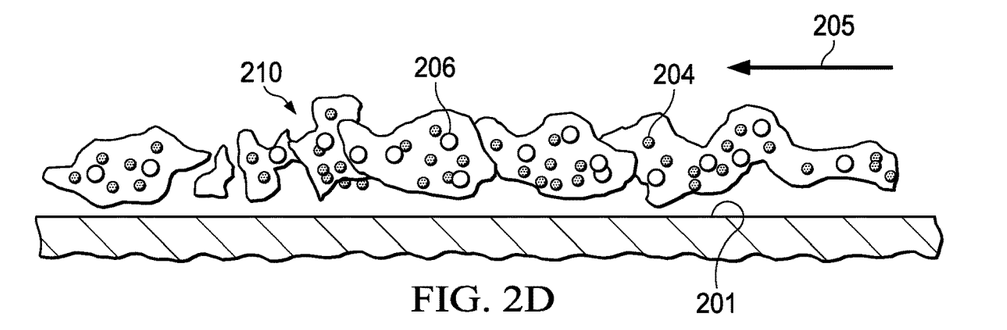
FIG. 2D is a schematic of a cross-section of a membrane filter of FIG. 2C after the biofilm on the surface of the membrane is ruptured by the oscillation of the acoustically excited encapsulated microbubbles and is uprooted by the flow of the feed solution.

FIGS. 2A-2D show cross-sections of the membrane (21-21) from the membrane filtration unit (100) as shown in FIG. 1. FIG. 2A shows a cross-section of the membrane without microbubbles present in the biofilm. FIG. 2B shows a cross-section of the membrane with microbubbles present in the biofilm prior to acoustic activation. FIG. 2C shows a cross-section of the membrane with microbubbles present in the biofilm during acoustic activation. FIG. 2D shows a cross-section of the membrane with microbubbles present in the biofilm following acoustic activation.

As shown in FIG. 2A, the feed solution stream (205) flows across the biofilm (203), which forms on the membrane surface (201). A normal biofilm is an aggregation of cellular microorganisms (204) and debris as well as extracellular polymeric substances (EPS). The boundary layer (202) is a hydrodynamic area of reduced feed solution flow adjacent the biofilm (203).

FIG. 2B shows a biofilm (203) on the membrane surface (201) formed in the presence of encapsulated microbubbles (206), which embed along with the microorganisms (204) within the biofilm (203). The encapsulated microbubbles (206) may be added to the feed solution stream (205) prior to the stream flow over the membrane surface (201). In FIG. 2B, the microbubbles (206) are embedded throughout the biofilm (203), but have not yet been acoustically activated. Microbubbles used in the present invention are usually sized less than 1 micrometer (μm), and preferably range in size from 0.5 μm to 10 μm for use in the present invention.

FIG. 2C shows a transducer (209) which applies sonic waves (208) to the surface of the membrane filtration unit at the resonate frequency of the encapsulated microbubbles (206). The application of sonic waves (208) to the biofilm (203) and membrane (201) acoustically excites the encapsulated microbubbles (206) embedded in the biofilm (203), causing the encapsulated microbubbles (206) to oscillate, rapidly expanding and contracting, without causing cavitation of the microbubbles (206). The oscillation of the microbubbles (206) causes disruption of the biofilm (203) from the membrane surface (201).

FIG. 2D shows the disrupted biofilm (210) detached from the membrane (201) following exposure to the sonic waves. The disrupted biofilm (210) is washed away from the membrane surface (201) by the feed solution stream (205). The microbubbles (206), which have returned to normal sizes, are carried away with the microorganisms (204). The ruptured biofilm (210) with microorganisms (204) and attached microbubbles (206) are part of the retentate that is prevented from passing through the membrane. Microbubbles used in the present invention are usually sized less than 1 micrometer (μm), and preferably range in size from 0.5 μm to 10 μm for use in the present invention.

Figure 3:
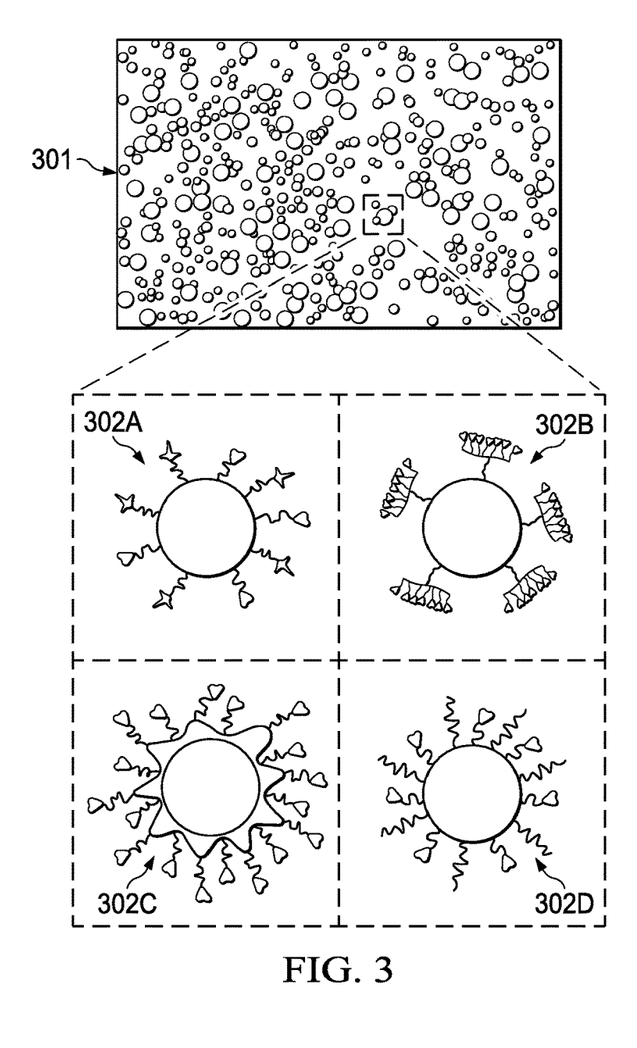
FIG. 3 is a micrograph of encapsulated microbubbles with schematics of encapsulated microbubbles having various shell structures.

FIG. 3 shows a micrograph of encapsulated microbubbles (301) with schematics (302A-D) of encapsulated microbubbles having various shell structures with ligands directed to specific types of binding. A ligand is a substance that binds to and forms a complex with a molecule. The ligands on the microbubble shells are able to bind to and form complexes with one or more extracellular polymeric substances (EPSs) in a biofilm on the membrane surface.

The low-frequency sound waves (ultrasound range) from the transducer drive the encapsulated microbubbles embedded in the biofilm structure to oscillate during expansion and contraction because of their compressible gas cores. Under resonating conditions, these encapsulated microbubbles rapidly expand and contract (approximately 5-10 times of initial radius) with oscillations, thus rupturing the biofilm from the membrane surface. The molecules bound to the ligands are affected by expansion and contraction of the oscillating microbubbles, leading to disruption of the biofilm from the membrane surface. The disrupted biofilm can then be washed away by the flow of the feed solution stream over the membrane surface.

Examples of ligands that are useful for encapsulated microbubbles of the present method are shown in FIG. 3, which include: a molecular adhesion ligand (302A), a polymeric ligand (302B), lipid coated ligands (302C), and buried ligands (302D) for nonspecific binding.

The encapsulated microbubbles (301) used herein comprise a gas core (e.g., air, or heavy gases like perfluorocarbon, or nitrogen) and an encapsulation shell comprising a lipid (302C) (e.g., mannosylerythritol lipids or the like), protein (302A) (e.g., serum such as Bovine serum, human serum, or the like) or polymer (302B) (e.g., poly-L-lysine, ethylene glycol, or the like), or other ligand (302D) capable of binding one or more extracellular polymeric substances (EPSs) in a biofilm.

The lipid, protein, polymer, or other ligand encapsulating the microbubbles binds one or more extracellular polymeric substances (EPSs) in a biofilm. The specific lipid, protein, polymer, or other ligand material forming the outer shell is selected based on the particular use. Furthermore, the encapsulation allows specific binding to the growing biofilm, provides stability to the gas core, and prevents coalescence of the microbubbles.

EXAMPLES

The examples below are intended to further illustrate certain aspects of the methods and compositions described herein, and are not intended to limit the scope of the claims.

Depending on the composition of the feed solution and the required quality of the product water, a combination of membrane or filtration processes may be appropriate. For example, if ultrapure water for certain industrial applications is required, a sequence of membrane filtration processes may be applied, such as reverse osmosis, ion exchanger, UV sterilization, and microfiltration as a point-of-use filter to remove traces of particles. In certain applications, such as the purification of industrial effluents and wastewaters or the desalination of brackish water, there may be a problem with the disposal of the concentrate. In these applications, brine post-treatment procedures may need to be applied to the concentrate.

Example 1

Example 1 is a general use description of the claimed method. The method is useful in a variety of membrane filtration systems including reverse osmosis systems, microfiltration systems, ultrafiltration systems, nano-filtration systems, forward osmosis systems, and membrane distillation systems. The membrane filtration system can be in any configuration (e.g., spiral wound, tubular, hollow fiber, flat sheet, etc.). The membrane filtration system can be submerged or pressurized. Microbubbles used in the present invention are usually sized less than 1 micrometer (μm), and preferably range from 5-50 microns in diameter size or from 0.5 μm to 10 μm for use in the present invention. Membrane thicknesses (while they depend on the system implementation) will range from 0.01 microns to 1000 microns, with 0.1 microns to 10 micron being a preferred thickness range for this example.

For this example, one or more filtrate and retentate ports are used, with each being sized approximately 7 mm×4.5 mm and 15 mm, respectively. An active surface area for the membrane is approximately 5 meters, with one or more membranes being used. Filtrate volume is approximately 12 liters, and retentate volume is approximately 8.75 liters, with a total volume in the membrane of approximately 20 liters when occupying the membrane filtration space. Low feed water flow rates for this example include relatively low feed water operating pressure are approximately 100 to 400 kPa (15 to 60 psi), while this system can be used with higher operating pressure of approximately 200 to 700 kPa (30 to 100 psi).

Encapsulated microbubbles in the size range of 10-20 microns are synthetized. These microbubbles are coated with an encapsulation shell primarily comprised of protein or polymeric ligands that have high affinity (e.g., in terms of charge and structure) to the extracellular polymeric substances (EPS) produced by the bacteria in the biofilm. The encapsulated microbubbles are dosed to the feed water which leads to the membrane filtration unit. The dosage of these microbubbles is intermittent (i.e., periodic, ranging from minutes, hours to days) or continuous.

Dosage methodology depends on several factors (e.g., binding efficiency, microbubble production rate, feed quality and microbubble production cost). When these microbubbles reach a biofilm formed on the membrane surface, the microbubbles are attracted to the biofilm due to structural and charge affinity and eventually get trapped inside the growing biofilm. Under normal operation, these microbubbles are an integral part of the growing biofilm. The microbubbles thus act as "moles" in the biofilm structure and will serve as a seed for rupturing the biofilm.

An acoustic (ultrasound) wave is applied to resonate the microbubbles. Given a size range of 10-20 microns, an ultrasound wave in the range of 400-700 KHz is used, depending on the applied pressure in the membrane system. An acoustic transducer is used to trigger required ultrasound waves for specified time frames. The acoustic pulse operates at the resonant frequency of the microbubble, causing the implanted microbubbles in the biofilm structure to grow and collapse and producing enough shear stress to rupture or traumatize the bacterial colony residing in the biofilm.

In cross-flow operation, hydrodynamic shear forces near the biofilm surface further aid in removing the biofilm uprooted by the microbubbles. This biofouling mitigation strategy is independent of the quality of the incoming feed water and therefore, reduces the need for pretreatment processes.

The retentate containing the uprooted biofilm contains microbubbles attached to the bacterial colony. Biofouling and biofilms accumulated on the membrane can include bacterial cells and a matrix of bacterially produced extracellular polymeric substances (EPS), along with biogenic and inorganic particles. Extracellular polymeric substances EPS, which are primarily composed of proteins, polysaccharides, and nucleic acids, plays a vital role in biofilm growth and development. As a result, the extracellular polymeric substances EPS can alter the density, porosity, charge, water content, and sorption properties of the biofilm with time.

After the membrane unit, these microbubbles return to their original size (10-20 microns) in the absence of ultrasound waves. The retentate is cleaned by exploding these microbubbles with high-intensity ultrasound waves in a collection tank (no membrane present). The high-intensity ultrasound drives the microbubbles to their acoustic cavitation thresholds and ultimately to sonoluminescence (extreme thermal shock, on a very short timescale), which traumatizes/kills nearby living cells.

By applying high-intensity ultrasound in the retentate collection tank, the bacteria and other undesirable microorganisms are killed, further improving retentate quality. The retentate is either reused in some percentage or is disposed. During cavitation and sonoluminescence, the microbubbles themselves are destroyed releasing the gas in the form of a jet structure. The treated retentate is thus free from gas bubbles and only shell material (e.g. protein or polymer) along with EPS and other organic/inorganic compounds remain.

Example 2

Example 2 is directed to a method of using the membrane filtration system and membranes of FIGS. 1 and 2A-2D, and reference numerals herein refer to the same elements depicted in FIGS. 1 and 2A-2D. This method is useful regardless of the quality of the feed source. The feed solution may be selected from the group consisting of fresh water, ground water, brackish water, sea water, waste water, and industrial water. By way of example, the methods provided herein for Example 2 are for water desalination and water reclamation/reuse systems.

As shown in FIG. 1, water in need of treatment, such as brackish water used in this example, enters the membrane filtration system (100) as part of the feed solution stream (10). Encapsulated microbubbles (15) having a compressed gas core with one or more ligands on the encapsulation shell that are selected for the specific type of EPS in the brackish water are synthesized in the microbubble production unit (11). The feed solution stream (10) flows adjacent the microbubble production unit (11) and the encapsulated microbubbles (15) are added to the feed solution stream (11). Microbubbles used in the present invention are usually sized less than 1 micrometer ($\mu$m), and preferably range from 5-50 microns in diameter size or from 0.5 $\mu$m to 10 $\mu$m for use in the present invention. Membrane thicknesses (while they depend on the system implementation) will range from 0.01 microns to 1000 microns, with 0.1 microns to 10 micron being a preferred thickness range for this example.

For this example, one or more filtrate and retentate ports are used, with each being sized approximately 7 mm×4.5 mm and 15 mm, respectively. An active surface area for the membrane is approximately 5 meters, with one or more membranes being used. Filtrate volume is approximately 12 liters, and retentate volume is approximately 8.75 liters, with a total volume in the membrane of approximately 20 liters when occupying the membrane filtration space. Low feed water flow rates for this example include relatively low feed water operating pressure are approximately 100 to 400 kPa (15 to 60 psi), while this system can be used with higher operating pressure of approximately 200 to 700 kPa (30 to 100 psi). The feed solution stream (11) and encapsulated microbubbles (15) flow into the mixing tank (12) where the baffles (14) within the mixing tank (12) cause turbulence in the feed solution leading to distribution of the encapsulated microbubbles (15) throughout the feed solution stream (10). The feed solution stream (10) and encapsulated microbubble (15) mixture exits the mixing tank (12) and flow toward the membrane filtration unit (30) via a stream flow outlet (13).

The feed solution stream (10) and encapsulated microbubble (15) mixture enters the membrane filtration unit (30) having a membrane (21) that is semipermeable and suitable for removing ions, molecules and other particles from brackish water by reverse osmosis. The feed solution stream (10) and encapsulated microbubble (15) mixture flows over the membrane (21).

As seen in FIG. 2B, inside the membrane filtration unit, the feed solution stream (205) with the encapsulated microbubbles flows over the membrane (201), and microorganisms (204) from the brackish water, such as bacteria, along with the encapsulated microbubbles (206), become embedded in biofilm (203) accumulating on the membrane surface (201). The hydrodynamic nature of the boundary layer (202) that exists at the interface of the biofilm (203) with the feed solution stream (205) inhibits the ability of the feed solution stream to flush materials away from the membrane surface (201) leading to an accumulation of microorganisms (204), microbubbles (206) and extracellular polymeric substances (EPS) that are part of the biofilm (203) adhered to the membrane surface (201).

Over time this accumulation of material can lead to biofouling, which is a reduction in the filtration capabilities of the membrane due to the build-up of biological materials on the membrane surfaces. Biofouling and biofilms accumulated on the membrane can include bacterial cells and a matrix of bacterially produced extracellular polymeric substances (EPS), along with biogenic and inorganic particles. Extracellular polymeric substances EPS, which are primarily composed of proteins, polysaccharides, and nucleic acids, plays a vital role in biofilm growth and development. As a result, the extracellular polymeric substances EPS can alter the density, porosity, charge, water content, and sorption properties of the biofilm with time.

At predetermined intervals of time, the transducer (209) is activated to produce sonic waves (208) causing oscillation of the encapsulated microbubbles (207). The oscillating microbubbles (207) expand and contract (approximately 5-10 times of initial radius), thus rupturing the biofilm (210) from the membrane surface (201). The frequency and amplitude of the acoustic waves are selected to cause rapid expansion and contraction of the microbubbles, but are not great enough to cause cavitation and rupture of the microbubbles.

When the sonic waves (208) are no longer contacting the encapsulated microbubbles (207), the expansion and contraction of the microbubbles will cease and the microbubbles will return to their original size. The ruptured biofilm (210), which is now detached from the membrane surface (201), contains the microorganisms (204), encapsulated microbubbles (206), and extracellular polymeric substances that made up the biofilm. The hydrodynamic boundary layer (202) is also reduced by the acoustic waves allowing the ruptured biofilm (210) to be washed away from the membrane surface (201) by the feed solution stream (205) as part of the retentate.

The retentate, containing the ruptured biofilm, and any materials excluded by the semipermeable membrane, such as ionic compounds like salt, will flow through the membrane filtration unit (30) and exit as the retentate stream (32). The permeate, from which the excluded materials have been removed, will exit the membrane filtration unit (30) as the permeate stream (31) and may be collected in a permeate collector (not shown in FIG. 1).

The retentate stream (32) flows into a retentate collector (40) which has a second acoustic transducer (20B) adjacent the retentate collector (40) capable of delivering sonic waves to the retentate in the collector. When activated, the transducer (20B) will produce ultrasonic waves of a frequency and amplitude sufficient to cause cavitation and rupture of the encapsulated microbubbles (15) and the sonic rupture of the microbubbles will also rupture the microorganisms in the retentate. The sonicated retentate will have extracellular polymeric substances left from the biofilm and the materials excluded by the membrane, but no longer has viable microorganisms or intact microbubbles.

The sonicated retentate will exit the retentate collector (40) via a retentate outlet (41) into a retentate line (42). The retentate line (42) carries the sonicated retentate to a retentate dumping station (44). From there, the retentate can be prepared for disposal, or the sonicated retentate can be recycled back into the feed solution stream (10) via a retentate recycle line (43).

The compounds and methods of the appended claims are not limited in scope by the specific compounds and methods described herein, which are intended as illustrations of a few aspects of the claims and any compounds and methods that are functionally equivalent are within the scope of this disclosure. Various modifications of the compounds and methods in addition to those shown and described herein are intended to fall within the scope of the appended claims.

Further, while only certain representative compounds, methods, examples and aspects of these compounds and methods are specifically described, other compounds and methods are intended to fall within the scope of the appended claims. Thus, a combination of steps, elements, components, or constituents can be explicitly mentioned herein; however, all other combinations of steps, elements, components, and constituents are included, even though not explicitly stated.

What is claimed is:

1. A method of reducing biofilm formation or removing biofilm in a membrane filtration system, the method comprising:

providing a feed solution to a membrane filtration system, wherein the feed solution comprises encapsulated microbubbles;

allowing the encapsulated microbubbles from the feed solution to fully embed, over time, in a biofilm in the membrane filtration system; and sonicating the encapsulated microbubbles, which are fully embedded in the biofilm on the membrane filtration system, at a frequency and amplitude that does not cause acoustic cavitation of the encapsulated microbubbles but oscillation between expansion and contraction to disrupt the biofilm.

2. The method of claim 1, wherein the encapsulated microbubbles comprise:

a gas core; and an encapsulation shell comprising a ligand, wherein the ligand binds one or more extracellular polymeric substances in the biofilm.

3. The method of claim 2, wherein the ligand is selected from the group consisting of a lipid, a protein, or a polymer.

4. The method of claim 1, wherein the membrane is a polymeric membrane or a ceramic membrane.

5. The method of claim 1, wherein the feed solution is selected from the group consisting of fresh water, ground water, brackish water, sea water, waste water, and industrial waste water.

6. The method of claim 1, wherein the membrane filtration system comprises one or more of the group consisting of a reverse osmosis system, a microfiltration system, an ultrafiltration system, a nanofiltration system, a forward osmosis system, and a membrane distillation system.

7. The method of claim 1, wherein the sonicating step comprises applying sonic waves with a transducer to the membrane filtration system at the resonance frequency of the encapsulated microbubbles.

8. The method of claim 7, wherein the sonicating step comprises applying ultrasonic waves to the membrane filtration system.

9. The method of claim 1, further comprising:

producing the encapsulated microbubbles; and supplying the produced encapsulated microbubbles to the feed solution by an encapsulated microbubble feed line.

10. The method of claim 9, further comprising:

collecting a retentate comprising the disrupted biofilm and the encapsulated microbubbles; and treating the retentate with ultrasonic waves, wherein the ultrasonic waves causes cavitation of the encapsulated microbubbles and sonoluminescence of the retentate.

* * * * *